United States Patent [19]

Lam et al.

[11] Patent Number: 5,145,956
[45] Date of Patent: Sep. 8, 1992

[54] METHOD FOR SEPARATION OF ANIONIC OLIGOSACCHARIDES

[75] Inventors: Lun H. Lam, Cupertino; David Tyrrell, Redwood Shores, both of Calif.

[73] Assignee: Glycomed Incorporated, Alameda, Calif.

[21] Appl. No.: 805,501

[22] Filed: Dec. 11, 1991

[51] Int. Cl.$^5$ .......................... C07H 1/06; C07H 3/10; C07H 19/00; C12N 11/08
[52] U.S. Cl. .................................. 536/124; 536/127; 436/807; 436/809
[58] Field of Search ................ 536/124, 127; 436/807, 436/809

[56] References Cited

U.S. PATENT DOCUMENTS

| | | | |
|---|---|---|---|
| 4,843,156 | 6/1989 | Miyake et al. | 536/127 |
| 4,927,752 | 5/1990 | Remacle | 436/807 |
| 5,023,330 | 6/1991 | Gander et al. | 536/124 |
| 5,031,449 | 7/1991 | Kuwana et al. | 422/70 |
| 5,034,520 | 7/1991 | Lormeau et al. | 536/127 |
| 5,045,535 | 9/1991 | Mang | 536/124 |
| 5,059,654 | 10/1991 | Hou et al. | |

*Primary Examiner*—Ronald W. Griffin
*Attorney, Agent, or Firm*—Kate H. Murashige; Gregory J. Giotta

[57] ABSTRACT

Separation of anionic oligosaccharides on a preparative scale with high resolution can be achieved by anionic exchange chromatography using PEI-derivatized supports.

10 Claims, 1 Drawing Sheet

METHOD FOR SEPARATION OF ANIONIC OLIGOSACCHARIDES

TECHNICAL FIELD

The invention relates to preparative procedures for separation of anionic oligosaccharides. More specifically, it concerns use of polyethyleneimine-coated supports to effect separations.

BACKGROUND ART

Anionic polysaccharides and oligosaccharides occur naturally in the form of glycosaminoglycans, such as heparin, dermatan sulfate, chondroitin sulfate, and the like. In addition, synthetic or natural carbohydrates can be converted to charge-bearing species by derivatization, especially to the multiplicity of free hydroxyl groups by, for example, sulfation. Oligosaccharides, as they occur natively, or fragments of these oligosaccharides, are notoriously difficult to separate on a preparative scale. Satisfactory resolution is sometimes achieved using such techniques as polyacrylamide gel electrophoresis or capillary zone electrophoresis, but, generally, only nanogram or microgram amounts can be obtained conveniently. This is inherent in the nature of capillary zone electrophoresis (Fujiwara, S., et al., *Anal Chem* (1987) 59:487–490; Al-Hakim, A., et al., *Anal Biochem* (1991) 195:68–73; Carney, S. L., et al., Ibid. 132–140). In the case of polyacrylamide gel electrophoresis, this low capability for recovery results from the necessity to use high concentrations of about 30–40% polyacrylamide in the gel (Rice, K. D., et al., *Biochem J* (1987) 244:515–522; Knudson, W., et al., *Biochemistry* (1984) 23:368–375). Another technique, reversed-phase ion-pairing HPLC, is inconvenient on a preparative scale because of the large amounts of organic solvents and ion-pairing reagent required to elute the oligosaccharides (Guo, Y., et al., *Analyt Biochem* (1989) 168:54–62; Guo, Y., et al., *Anal Biochem* (1989) 175:96–104).

Anion exchange has also been used for oligosaccharide separation in the context of HPLC using "strong" anion-exchange supports containing quarternary amine functional groups (Bienkowski, M. J., et al., *J Biochem* (1985) 260:256–265; Merchant, Z. M., et al., *Biochem J* (985) 229:369–378). The problem with strong anion-exchange supports resides in poor resolution and the need for high salt concentrations to elute the adsorbed anionic oligosaccharides. However, cellulose supported anionic exchange supports have been used to remove heparin from blood plasma (EP application 281,128).

It has now been found, surprisingly, that supports coated with polyethyleneimine (PEI) provide excellent resolution of anionic carbohydrates on a preparative scale. While PEI-coated supports have been used for separation of peptides and proteins and for oligonucleotide separations, the only use of any similar technique with respect to anionic oligosaccharides has been with respect to thin-layer chromatography, i.e., for analytical, not preparative, purposes (Ram, P. A. et al., *Anal Biochem* (1989) 178:421–426; Zagrod, M. E. et al., *Invest Opthamol Vis Sci* (1985) 26:1475–1473). PEI has also been used as a detection for histological staining to determine the presence of anionic substances, including heparin in biological samples. See, for example, Whiteside, C. et al., *Lab Invest* (1989) 61:650–660; Spooner, B. S. et al., *Arch Oral Biol* (1989) 34:541–549. PEI, including PEI cross-linked with diisocyanate has been used to precipitate heparin or other polysaccharides from solution. See, e.g., Belgian patent 888463. To applicants, knowledge, PEI-coated chromatographic supports have not previously been used for either analytic or preparative separation of oligosaccharides.

DISCLOSURE OF THE INVENTION

The invention provides a method to separate anionic oligosaccharides that results in excellent resolution of these saccharides on a preparative scale. Sufficient amounts (i.e., mg quantities) of highly resolved fractions are provided to permit sequence determination on the purified compositions.

Thus, in one aspect, the invention is directed to a method to separate the components of a mixture of anionic oligosaccharides, which method comprises applying a mixture of said anionic oligosaccharides to a chromatographic column, said column comprising a solid support being coated with polyethyleneimine (PEI) under conditions wherein the anionic oligosaccharides of the mixture are adsorbed, and, eluting said anionic oligosaccharides from the column so as to obtain a multiplicity of fractions containing the various components of the mixture.

In other aspects, the invention is directed to methods to modify said PEI support to accommodate carbonyl-containing oligosaccharides and to methods of separating mixtures of said oligosaccharides using the modified columns.

MODES OF CARRYING OUT THE INVENTION

Figure 1A:
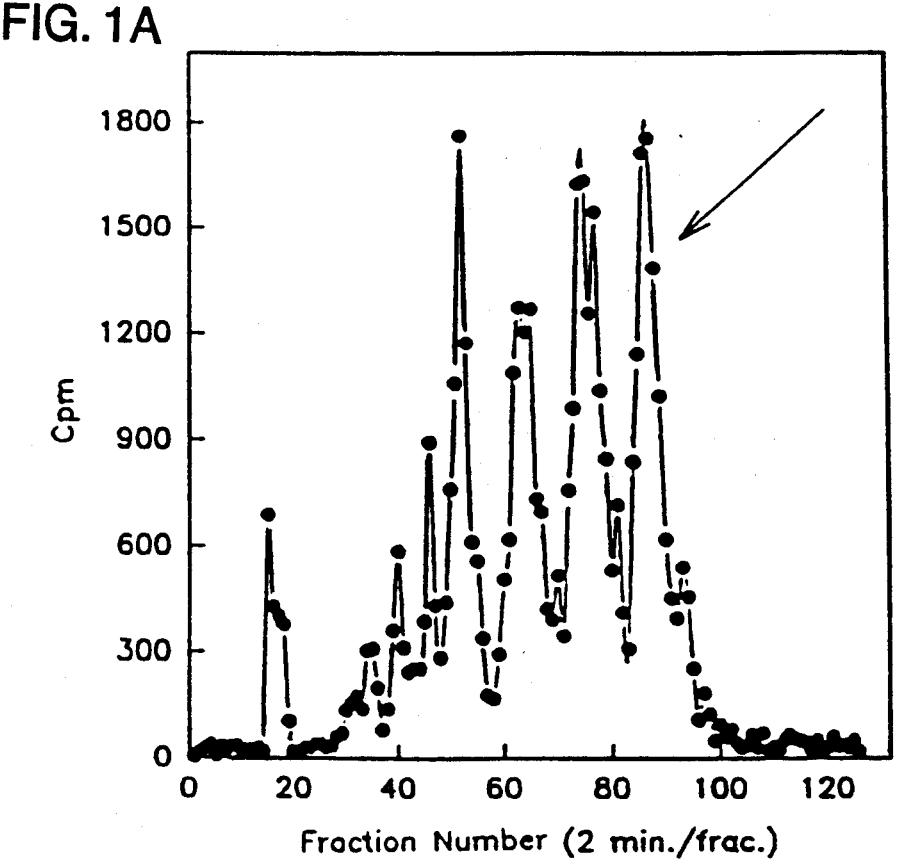
FIGS. 1A and 1B show a typical elution pattern from a PEI column with respect to a mixture of borohydride/borotritide-reduced hexasaccharides derived from nitrous acid-depolymerized heparin.

The anionic oligosaccharides which are suitable candidates for separation according to the method of the invention may be derived from any source, but the problem of their separation most typically arises in the context of separation of fragments obtained by depolymerization of glycosaminoglycans. Glycosaminoglycans are polysulfated polysaccharides containing alternating uronic acid and glycosamine residues. Various forms of these glycosaminoglycans (GAGs) are defined by the nature of the uronic acid and glycosamine residues, and by the degree and nature of the sulfation. In general, GAGs, even those sharing the same generic name, such as dermatan sulfate, chondroitan sulfate, heparan sulfate, or heparin are heterogeneous mixtures, and consist of polymers with imperfectly repeating subunits. Thus, fragmentation of these GAGs leads, in general, to a mixture of oligosaccharides with varying degrees of sulfation and varying size. A preliminary size separation procedure is often useful, but preparative separation of the members of the size-separated group based on degree of sulfation has often been difficult. The method of the invention is particularly useful in this regard.

While the foregoing paragraph describes the context in which the method of the invention is particularly applicable, the invention method is available to solve the problem associated with the requirement to separate the components of a mixture of anionic oligosaccharides, regardless of the origin of the mixture. For example, oligosaccharides, synthetic or native, may be sulfated in vitro, generally resulting in a heterogeneous mixture with varying degrees of sulfation. The components of these mixtures may also be separated using the method of the invention.

In general, the invention method comprises applying the mixture of anionic oligosaccharides to a chromatographic support which is characterized by containing a surface comprised of polyethyleneimine (PEI). Such supports are commercially available, for example, from Rainin Instrument Company under the name "Hydropore AX", which is a PEI-coated silica gel, and from BioRad Laboratories under the name "Biogel MA7P", which contains PEI coated to nonporous beads. The PEI coating is obtained by polymerization of the ethyleneimine monomer, resulting in generation of amino groups, including primary, secondary and tertiary amines. Thus, the resulting PEI-coated support contains a range of cationic residues to provide the basis for anion exchange.

As defined herein, "PEI" refers to a polymer obtained by polymerization of the monomer ethyleneimine to obtain a polymer with a multiplicity of amino groups, which are representative of a range of primary, secondary, and tertiary amines, in a manner analogous to that characterizing commercially available PEI-derivatized supports. These polymers offer a range of Ka values for the pendant amines. Modified forms of these PEI supports, such as forms that are further cross-linked with diisocyanate, are also included in this definition.

The PEI-coated supports may be used as provided for those oligosaccharides which have been treated with reducing agent to convert carbonyl groups to alcohols. This technique, using metal hydrides, is well known in the art and is a routine matter. Alternatively, the unreduced oligosaccharides may be separated by the method of the invention by modifying the PEI coating. This is done by pretreating the PEI coating with a low molecular weight aldehyde or ketone to derivatize the primary amino groups on the support. The thus-protected support can be used for separation of the nonreduced oligosaccharides.

The PEI-coated support is loaded into a chromatographic column of suitable dimensions, depending on the nature of the sample and the quantity of components of the mixtures to be separated. Appropriate sizing of columns depending on the quantities to be separated is a routine procedure. The PEI column is preequilibrated most conveniently with distilled water. The mixture is then applied to the column, generally dissolved in distilled water, under conditions wherein the anionic components of the mixture are adsorbed to the column. The column is then eluted using a salt gradient, preferably a salt such as ammonium bicarbonate, which can be removed by evaporation or lyophilization. Typical salt gradients are 0–2M, preferably 0–1M. The precise range of the gradient will, of course, depend on the nature of the components and the number of components in the mixture.

Elution is conducted so as to generate a multiplicity of fractions, which can then be assayed for the presence of the various components using an appropriate assay method, such as uronic acid assay, hexosamine assay or phenol-sulfuric acid assay depending on the nature of the sugars. In some instances, it is possible to label the components of the mixture and to determine the content of the fractions by the amount of label. For example, tritiated reduced oligosaccharides may be used in the starting mixture, and tritium-containing fractions determined by scintillation counting.

The foregoing methods provide excellent resolution of preparative quantities of oligosaccharides. In preferred protocols, the components are first size-separated to constitute mixtures of uniform molecular weight, such as hexasaccharides, tetrasaccharides, pentasaccharides, decasaccharides, etc.

The following examples are intended to illustrate but not to limit the invention.

PREPARATION A

DEPOLYMERIZATION OF HEPARIN

Heparin (10 g) and 345 g sodium nitrite were dissolved in 80 ml water at pH 6. The pH of the solution was adjusted to 1.5 with 6N HCl and maintained by dropwise addition of either 6N HCl or 2M sodium carbonate. The reaction was maintained until completion was reached, as shown by the cessation of nitrogen evolution. In general, the time required was approximately 6 minutes. The pH was then adjusted to 7.5 with 2M sodium carbonate and 1.26 grans of sodium borohydride/borotritide were added to reduce carbonyl groups. After incubating 60 mins at 50° C., excess borohydride was destroyed by dropwise addition of 6M HCl until a pH of 4.0 was attained. After incubating another 60 min at room temperature, the pH was adjusted to 7.0 with 2M sodium carbonate. The solution of reduced heparin fragments was then degassed under vacuum, and concentrated by lyophilization or rotary evaporation to a concentration of 300 mg heparin fragment/ml. The preparation process is scalable.

The concentrated mixture was then chromatographed on a Biogel P10 system containing two columns in tandem, each approximately 5 cm × 128 cm and containing a total of 5 l of Biogel P10. The columns were packed and run in 0.5M ammonium bicarbonate at a flow rate of 0.7 ml/min. Fractions of 18 ml each were analyzed for oligosaccharides using the carbazole procedure of Bitter, T., and Muir, H. M., *Anal Biochem* (962) 4:330–334. The saccharides elute sequentially by size, largest first; the last peak contains mostly disaccharides. A pool of fragments containing hexasaccharides was recovered.

EXAMPLE 1

SEPARATION OF REDUCED HEXASACCHARIDES

Figure 1B:
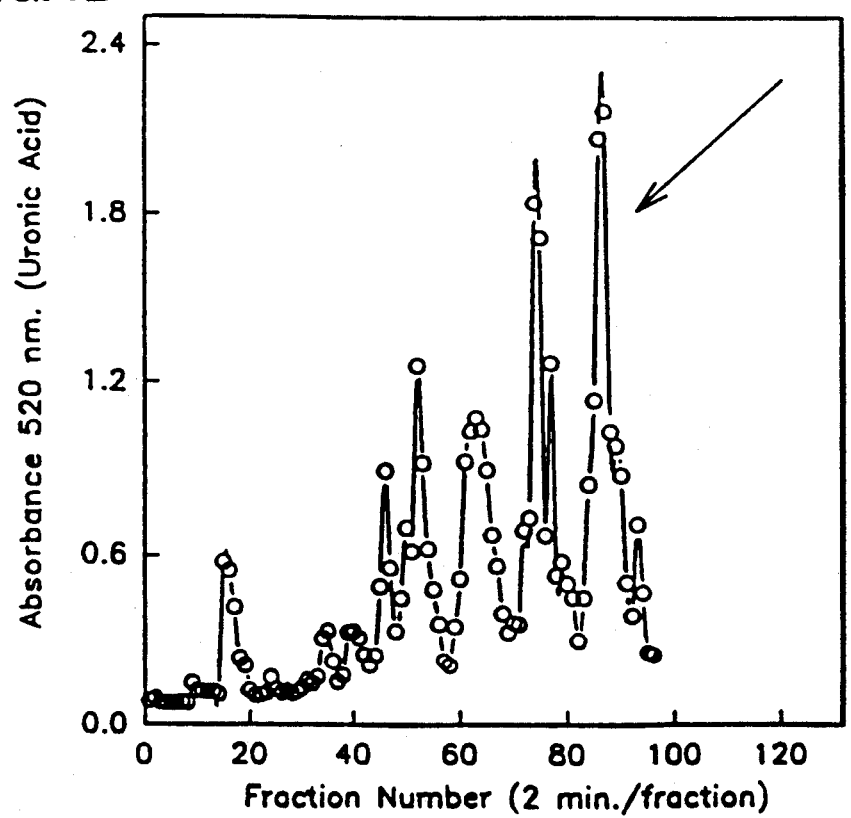

A solution containing 1 mg of the mixture of reduced tritiated hexasaccharides prepared as described in Preparation A was applied to a Biogel MA7P column (7.8 × 50 mm in tandem with 10 × 250 mm) which had been preequilibrated and washed with distilled water. After discarding the flow-through volume, the column was eluted using a gradient of 0–1M ammonium bicarbonate at a flow rate of 0.5 ml/min, and fractions were collected every two minutes. The gradient was applied so as to increase the concentration of ammonium bicarbonate over the 0–1M range over a time period of 264 minutes. The results are shown in FIG. 1.

Panel A shows the elution pattern as determined by scintillation counting of the labeled components; FIG. 1, Panel B, shows the corresponding pattern as determined by uronic acid assay. The uronic assay is conducted as described by Bitter, T. and Muir, H. M., *Anal Biochem* (1962) 4:330–334.

We claim:

1. A method to separate components of a mixture of anionic oligosaccharides lacking carbonyl groups, which method comprises:

applying said mixture to a chromatographic column wherein said chromatographic column contains a solid support coated with polyethyleneimine (PEI) under conditions where said anionic oligosaccharides are adsorbed to the column;

followed by eluting said column with a salt gradient to obtain a multiplicity of fractions so as to separate said anionic oligosaccharide components.

2. The method of claim 1 wherein said mixture contains anionic oligosaccharides of substantially the same molecular weight.

3. The method of claim 1 wherein said anionic oligosaccharides are obtained by depolymerization of a glycosaminoglycan.

4. The method of claim 3 wherein said glycosaminoglycan is heparin.

5. The method of claim 1 wherein said salt gradient elution is conducted using a lyophilizable salt.

6. The method of claim 5 wherein said salt is ammonium bicarbonate.

7. The method of claim 1 wherein said anionic oligosaccharides have been prepared by reduction of carbonyl-containing oligosaccharides with a metal hydride.

8. A method to modify a chromatographic support coated with polyethyleneimine (PEI), which method comprises treating said support with a low molecular weight aldehyde in an amount and for a time sufficient to block primary amino groups contained in said PEI, followed by removing excess aldehyde from the support.

9. A chromatographic support prepared by the method of claim 8.

10. A method to separate components of a mixture of anionic oligosaccharides at least some of which contain carbonyl groups, which method comprises:

applying said mixture to a chromatographic column wherein said chromatographic column contains a solid support coated with polyethyleneimine (PEI) modified by the method of claim 8 under conditions where said anionic oligosaccharides are adsorbed to the column;

followed by eluting said column with a salt gradient to obtain a multiplicity of fractions so as to separate said anionic oligosaccharide components.

* * * * *